US008309141B2

(12) United States Patent
Liu et al.

(10) Patent No.: US 8,309,141 B2
(45) Date of Patent: *Nov. 13, 2012

(54) HERBAL COMPOSITION PHY906 AND ITS USE IN CHEMOTHERAPY

(75) Inventors: Shwu-Huey Liu, Madison, CT (US); Zaoli Jiang, Woodbridge, CT (US); Yung-Chi Cheng, Woodbridge, CT (US)

(73) Assignee: Yale University, New Haven, CT (US)

( * ) Notice: Subject to any disclaimer, the term of this patent is extended or adjusted under 35 U.S.C. 154(b) by 164 days.

This patent is subject to a terminal disclaimer.

(21) Appl. No.: 12/527,302

(22) PCT Filed: Feb. 14, 2008

(86) PCT No.: PCT/US2008/053965
§ 371 (c)(1),
(2), (4) Date: Jan. 29, 2010

(87) PCT Pub. No.: WO2008/101079
PCT Pub. Date: Aug. 21, 2008

(65) Prior Publication Data
US 2010/0255129 A9    Oct. 7, 2010

Related U.S. Application Data

(63) Continuation-in-part of application No. 11/100,433, filed on Apr. 7, 2005, now Pat. No. 7,534,455, which is a continuation-in-part of application No. 10/220,876, filed as application No. PCT/US01/07353 on Mar. 8, 2001, now Pat. No. 7,025,993, which is a continuation-in-part of application No. 09/522,055, filed on Mar. 9, 2000, now abandoned.

(60) Provisional application No. 60/901,310, filed on Feb. 15, 2007, provisional application No. 60/625,943, filed on Nov. 9, 2004.

(51) Int. Cl.
A61K 36/00     (2006.01)
A61K 36/725    (2006.01)
A61K 36/539    (2006.01)
A61K 36/65     (2006.01)

(52) U.S. Cl. ..................................................... 424/725
(58) Field of Classification Search .................. None
See application file for complete search history.

(56) References Cited

U.S. PATENT DOCUMENTS
4,613,591 A    9/1986    Aburada et al.
(Continued)

FOREIGN PATENT DOCUMENTS
EP    0943620 A2    9/1999
(Continued)

OTHER PUBLICATIONS
H.B. MacPhillamy; Plant Science Bulletin, Apr. 1963, vol. 9, Issue 2, pp. 1-15.*
(Continued)

Primary Examiner — Patricia Leith
(74) Attorney, Agent, or Firm — Kenyon & Kenyon LLP

(57) ABSTRACT

This invention provides herbal compositions useful for increasing the therapeutic index of chemotherapeutic compounds. This invention also provides methods useful for improving the quality of life of an individual undergoing chemotherapy. Furthermore, this invention improves the treatment of disease by increasing the therapeutic index of chemotherapy drugs by administering the herbal composition PHY906 to a mammal undergoing such chemotherapy.

30 Claims, 12 Drawing Sheets

U.S. PATENT DOCUMENTS

| | | | |
|---|---|---|---|
| 4,618,495 | A | 10/1986 | Okuda et al. |
| 5,414,015 | A | 5/1995 | Konoshima et al. |
| 5,437,866 | A | 8/1995 | Sun |
| 5,552,440 | A * | 9/1996 | Crooks et al. ............... 514/553 |
| 5,595,756 | A * | 1/1997 | Bally et al. .................. 424/450 |
| 5,665,393 | A | 9/1997 | Chen et al. |
| 6,048,847 | A | 4/2000 | Ramadoss et al. |
| 6,630,176 | B2 | 10/2003 | Li et al. |
| 7,025,993 | B2 * | 4/2006 | Cheng et al. ................. 424/725 |
| 7,534,455 | B2 * | 5/2009 | Cheng et al. ................. 424/725 |
| 2003/0111180 | A1 * | 6/2003 | Nagahata et al. ........ 156/345.47 |
| 2003/0157126 | A1 * | 8/2003 | Li et al. .................. 424/195.15 |
| 2005/0196473 | A1 | 9/2005 | Cheng et al. |

FOREIGN PATENT DOCUMENTS

| | | |
|---|---|---|
| WO | WO 01/66123 | 9/2001 |
| WO | WO 2006/053049 | 5/2006 |
| WO | WO 2008/101079 | 8/2008 |

OTHER PUBLICATIONS

Raskin et al. Can an Apple a Day Keep the Doctor Away? Current Pharmaceutical Design, 2004, 10, pp. 3419-3429.*

Liu, Shwu Huey et al., "Prevention of CPT-11 Induced Toxicity by a Chinese Medicinal Formulation, PHY-906", Proceedings of the American Association for Cancer Research Annual, No. 41, Mar. 2000, p. 410.

Liu, Shwu Huey et al., "A Chinese Medicine Formulation, PHY-906, Can Enhance the Therapeutic Index of CPT-11 and other Anticancer Druges Against Cancer in Mice", Proceedings of the American Association for Cancer Research Annual, vol. 42, Mar. 2001, p. 85.

M. Narita et al., "Inhibition of Beta-Glucuronidase by Natural Glucurondes of Kampo Medicines Using Glucuronide of SN-38(7-Ethyl-10-Hydroxycamptothecin) as a Substrate", Xenobiotia, vol. 23, No. 1, 1993, p. 5-10.

Takasuna et al., "Protective Effects of Kampo Medicines and Baicalin Against Intestinal Toxicity of a New Anticancer Camptothecin Derivative, Irinotecan Hydrochloride (CPT-11), in Rats", Japanese Journal of Cancer Research, vol. 86, No. 10, 1995, p. 978-984.

K. Mori et al., "Kampo Medicines for the Prevention of Irinotecan-Induced Diarrhea in Advanced Non-Small cell Lung Cancer", Gan T. Kagaku Ryoho Japanese Journal of Cancer and Chemotherapy, Jul. 1998, 25(8): 1159-1163.

R.M. Goldberg et al., "IrinotecanPlus 5-Fu and Leucovorin in Advanced Colorectal Cancer: North American Trials", Oncology, S. Karger Ag, Basel, CH, vol. Suppl. 6. No. 6, Aug. 1998, p. 59-63.

Bleiberg H., European J. of Cancer, 35(3): 371-379, 1999.

Govindarajan et al., Lancet, 356:566, Aug. 12, 2000.

Stucky-Marshall L., Cancer Nursing, 22(3):212, 1999.

Suzuki et al, Supressor Macrophages: A Role on the Growth of Transplanted Tumors and Regulation by an Extract of Licorice, Glycyrrhizin; Oncologia (Tokyo) 1987, 20(5), pp. 124-133 (abstract).

Raskin et al., "Can an Apple a Day Keep the Doctor Away?" Current Pharmaceutical Design, 2004, 10; pp. 3419-3429.

H.B. MacPhillamy; Plant Science Bulletin; Apr. 1963, vol. 9, Issue 2, pp. 1-15.

Liu, Shwu Huey et al., "Developing PHY-906 as a Broad-Spectrum Modulator of Chemotherapeutic Agents in Cancer Therapy", Proceedings of the Annual Meeting of the American Association for Cancer Research, vol. 45, Mar. 2004, p. 128.

Nagai et al., "Antiviral Activity of Plant Flavonoid, 5,7,4'-Trihydrozy-8-methoxyflavone, from the Roots of *Scutellaria baicalensis* against Influenza A (H3N2) and B Viruses", T et al., Biol Pharm Bull, 1995, 18(2): 295-9.

Huang, L et al., Zhonggou Zhong Yao Za Zhi, 1990, 15(2): 115-7, 128.

Hande, et al., "Metabolism and Excretion of Etoposide in Isolated, Perfused Rat Liver Models", Cancer Res. 1988, vol. 48, No. 20, p. 5692-5695.

Sommadossi, et al., "Modulation of 5-Fluorouracil Catabolism in Isolated Rat Hepatocytes with Enhancement of 5-Fluorouracil Glucoronide Formation", Cancer Res. 1985, vol. 45, No. 1, p. 116-121.

Certain Chinese Herbal Medicine Prescriptions, 1979.

Yogatrangini by Trimalla Bhatta—Commentary by Duttarama Mathura; Chaukhamba Vidyabhavan, Varanasi, Edn. Reprint 2003, p. 169; F.ID: RG/4478; Form.name: Badarikalkah ("Third party observation" re EP2005826289).

Bogar 700 by Bogar, Ed. Ramachandran, Pub: Thamarai Noolagam Chennai (1994), p. 8-13; F.ID: PD03/02; Form. name: Maha Mega Rasangam ("Third party observation" re EP2005826289).

Li, Ronghua et al.,"Evaluation of Clinical Efficacy and Review on Progress of Antineoplastic Drugs," Evaluation and Analysis of Drug-use in Hospital of China, 2004, vol. 4, No. 1 (in Chinese language, English language abstract).

Li, Dong, "Progress on Clinical Application of Thalidomide," Chinese Journal of Clinical Pharmacy, 2004, vol. 13, No. 2.

Saif, M. W., et al., Phase I study of the botanical formulation PHY906 with capecitabine in advanced pancreatic and other gastrointestinal malignancies. Phytomedicine (2010), doi:10.1016/j.phymed.2009.12.016.

Yen, Y., et al., Phase I/II Study of PHY906/Capecitabine in Advanced Hepatocellular Carcinoma, Anticancer Research 29: 4083-4092 (2009).

* cited by examiner

HERBAL COMPOSITION PHY906 AND ITS USE IN CHEMOTHERAPY

CROSS-REFERENCE TO RELATED APPLICATIONS

This application is a U.S. National Stage application of International Application number PCT/US200S/053965, filed on Feb. 14, 2008, which claims the benefit of U.S. Provisional Patent Application Ser. No. 60/901,310, filed on Feb. 15, 2007, the contents of which are herein incorporated by reference in their entirety for all purposes. This application also claims the benefit under 35 U.S.C. §120 as a Continuation-in-Part application of U.S. patent application Ser. No. 11/100,433 filed Apr. 7, 2005, now U.S. Pat. No. 7,534,455, which claims the benefit of U.S. Provisional Patent Application Ser. No. 60/625,943 filed Nov. 9, 2004, and which also claims the benefit under 35 U.S.C. §120 as a Continuation-in-Part of U.S. patent application Ser. No. 10/220,876 filed Sep. 30, 2002, now U.S. Pat. No. 7,025,993, which is a U.S. National Stage application of International Application No. PCT/US2001/007353 filed Mar. 8, 2001, which in turn, is a Continuation-in-Part of U.S. patent application Ser. No. 09/522,055 filed Mar. 9, 2000 and now abandoned, the contents of which are herein incorporated by reference in their entirety for all purposes. This application herein incorporates by reference the contents of International Application No. PCT/US2005/040605 filed Nov. 9, 2005, in its entirety.

FIELD OF THE INVENTION

The present invention relates to herbal compositions and the use of them for enhancing the therapeutic effects of chemotherapeutic compounds.

BACKGROUND OF THE INVENTION

Cancer remains one of the major cause of death around the world. Specifically, cancer is the second overall cause of death in the United States. Gastrointestinal cancers, including colorectal, liver, and pancreatic cancers, are of particular concerns not only because of their high incidence rates, but also because of their high mortality rate, especially in pancreatic and liver cancer patients (1-4). From years 1992-1999, studies revealed that the five-year relative survival rate of colorectal cancer was 62.3% while that of liver cancer was 6.9% and 4.4% for pancreatic cancer. The median survival of liver cancer was 3.5 weeks to 6 months while it was 4 to 6 months for pancreatic cancer (3). With only very poor chemotherapeutic regimens available, pancreatic cancer has the highest mortality rate among all cancers in the United States, with a less than 5% survival rate 5 years from diagnosis (3). Although several regimens are currently used in clinical trials for hepatocellular carcinoma, there is no FDA-approved chemotherapeutic agent available. The low survival rates for both pancreatic and hepatocellular cancers are attributed to many factors including diagnosis is difficult, the tumor growth is highly aggressive, surgical removal of tumor is of low probability, and the tumor has a high rate of chemotherapy resistance.

SUMMARY OF THE INVENTION

Figure 1:
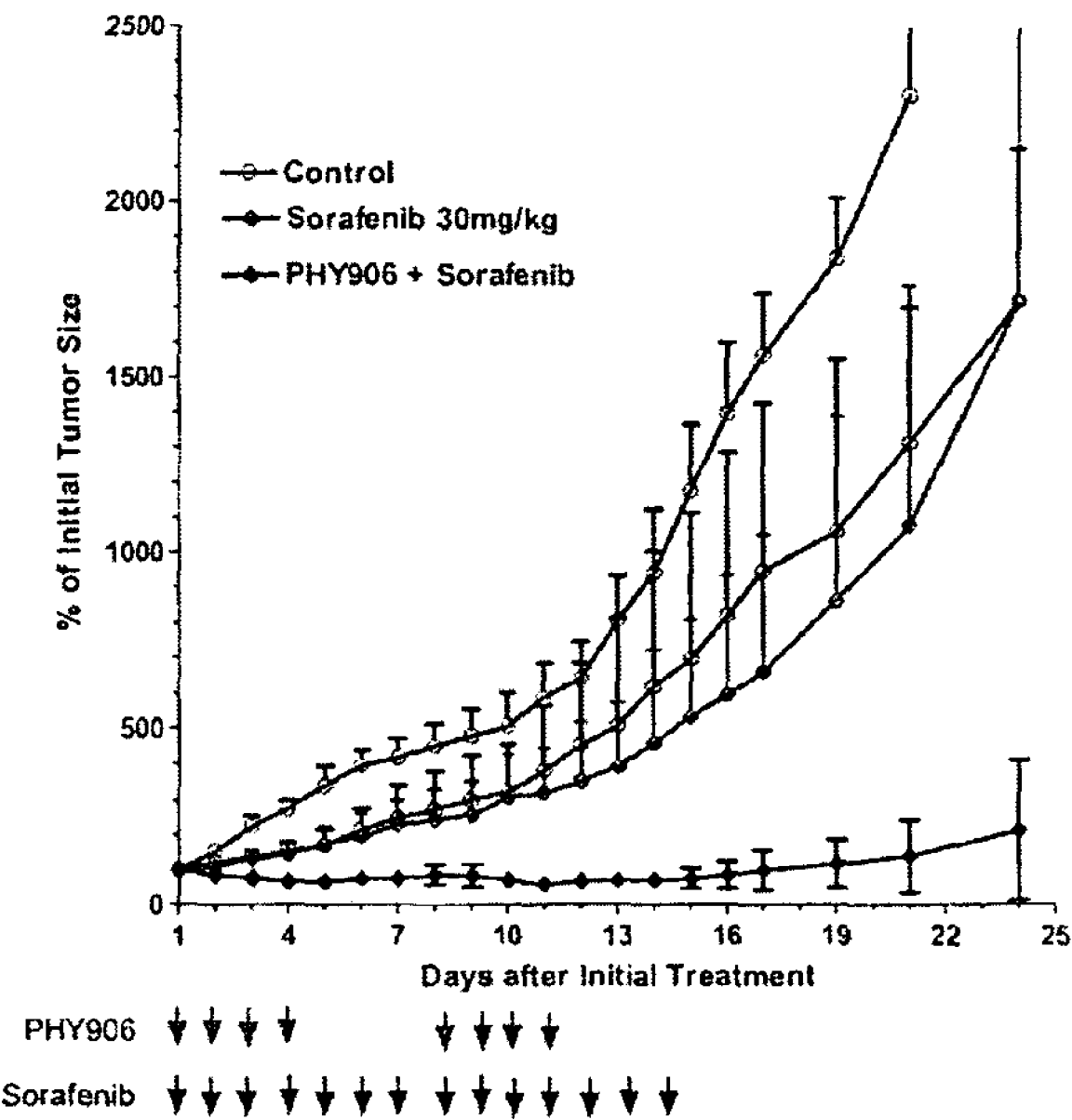
FIG. 1 shows the effect of PHY906 (500 mg/kg, bid, D1-4 and 8-11) on tumor growth in Sorafenib (30 mg/kg, pig, bid, D1-14)-treated BDF-1 mouse bearing mouse colon 38 tumors. Sorafenib (30 mg/kg) was given orally twice a day for a consecutive 14 days. PHY906 (500 mg/kg) was given orally 30 min before sorafenib twice a day on days 1-4 and days 8-11 (N=5 in each group).

In one aspect, the present invention provides a composition comprising: i) pharmaceutically acceptable carrier; ii) an herbal preparation comprising Scutellaria, Glycyrrhiza, Ziziphus, and Paeonia; and iii) one or more chemotherapeutic compounds.

This invention provides the herbal composition PHY906 combined with a pharmaceutically acceptable carrier and optionally including one or more chemotherapeutic compounds or antiviral agents. The four plant species which are chosen to make a particular formulation of PHY906 are each selected from one of four different groups of herbs: Scutellaria, Licorice, Peony Alba and Ziziphi fruit. The herbs are chosen so as to obtain one or more of the desirable attributes of PHY906, wherein such attributes include, but are not limited to, increasing the therapeutic index of one or more chemotherapeutic compounds, enhancing the antitumor activity of one or more chemotherapeutic compounds or enhancing the antiviral activity of one or more antiviral agents, modulating hematopoietic activity, modulating hematological and immunological activity, and improving the quality of life of a mammal undergoing chemotherapy or antiviral therapy. In some embodiments, the present invention provides compositions comprising: i) a pharmaceutically acceptable carrier; ii) an herbal preparation comprising Scutellaria, Glycyrrhiza, Ziziphus and Paeonia; and iii) a chemotherapeutic formulation.

In some embodiments, the herbal preparation consists of Scutellaria baicalensis, Glycyrrhiza uralensis, Ziziphus jujuba, and Paeonia lactiflora. In some embodiments, the compositions consist essentially of a pharmaceutically acceptable carrier and material from a plant species of each of the following genera of herbs: Scutellaria, Glycyrrhiza, Ziziphus and Paeonia.

The present invention provides methods of modulating hematopoietic activity for the treatment of a disease by administering to a mammal in need of such treatment a therapeutically effective amount of a composition consisting essentially of a pharmaceutically acceptable carrier and material or chemical from or herbal preparation comprising a plant species of each of the following genera of herbs: Scutellaria, Glycyrrhiza, Ziziphus and Paeonia.

In another aspect, the present invention provides a method of treating a disease in a mammal in need thereof comprising administering a therapeutically effective amount of a composition comprising: i) a pharmaceutically acceptable carrier; ii) an herbal preparation comprising Scutellaria, Glycyrrhiza, Ziziphus, and Paeonia; and iii) one or more chemotherapeutic compounds.

In another aspect, the present invention provides a method of increasing the therapeutic index of cancer therapeutic compounds for the treatment of cancer by administering to a mammal in need thereof, a therapeutically effective amount of a composition comprising a pharmaceutically acceptable carrier, and an herbal preparation comprising Scutellaria, Glycyrrhiza, Ziziphus, and Paeonia.

In yet another aspect, the present invention provides a method of relieving side effects of a chemotherapeutic compound in a mammal comprising administering a composition comprising: i) a pharmaceutically acceptable carrier; ii) an herbal preparation comprising Scutellaria, Glycyrrhiza, Ziziphus, and Paeonia; and iii) one or more chemotherapeutic compounds.

In yet another aspect, the present invention provides a method of improving the quality of life of a mammal undergoing chemotherapy which comprises administering a therapeutically effective amount of one or lore chemotherapeutic compounds and a composition comprising: i) a pharmaceutically acceptable carrier; an herbal preparation comprising Scutellaria, Glycyrrhiza, Ziziphus, and Paeonia; and iii) one or more chemotherapeutic compounds.

DETAILED DESCRIPTION OF THE INVENTION

Gemcitabine is the only clinically approved chemotherapeutic agent for pancreatic cancer; however, the response rate in patients to gemcitabine is only 6-11% and the overall survival time is generally 4-6 months. Gemcitabine is a nucleoside analog with two mechanisms of action, including the inhibition of ribonucleotide reductase, an enzyme that converts nucleotide diphosphate to deoxynucleotide triphosphate and that is required for DNA synthesis and that competes with deoxycytidine triphosphate as a fraudulent base in DNA synthesis(3,5-10). With the low response and survival rates of gemcitabine monotherapy, several gemcitabine-combination drug regimens have been tested clinically for improving therapeutic efficacy. These trials include gemcitabine with other commonly used and FDA-approved anticancer drugs including CPT-11, capecitabine, and oxaliplatin (11-14). Unfortunately, no satisfactory combination drug regimens have been discovered and an effective regimen for pancreatic cancer is urgently needed.

Capecitabine (Xeloda), an oral fluoropyrimidine, is a rationally designed oral prodrug efficiently absorbed from the gastrointestinal tract and converted to 5-FU, preferentially in neoplastic tissues. It has been approved by the FDA as a first-line chemotherapy for the treatment of colorectal and breast cancers with reduced toxicities (15-17). Capecitabine has also shown promising antitumor activity as a single agent in pancreatic cancer (18) and liver cancer (19).

Hepatocellular carcinoma (HCC) is currently treated by surgical procedures and chemotherapy. Surgical removal and postoperative therapies may improve the outlook for some patients. Unfortunately, the vast majority of patients with hepatocellular carcinoma will have unresectable cancers. In late 2007, sorafenib became the first FDA-approved chemotherapeutic agent for HCC. Published clinical studies indicate significant anti-tumor effects (20,21). Oral multikinase inhibitor sorafenib (BAY 43-9006) has a dual-action on Raf kinase and vascular endothelial growth factor. Sorafenib prevents tumor growth by combining inhibition in tumor cell proliferation and tumor angiogenesis. Preclinical studies suggest that sorafenib may offer therapeutic benefits in HCC by blocking Raf-1 signal transduction pathway.

Colorectal cancer has been reported to be the third most common cause of death from cancer in the United States (22). Recently, the FDA approved the triple combination use of Oxaliplatin/5-FU/LV as the first-line treatment for patients with advanced colorectal cancer. Oxaliplatin is a synthesized diaminocyclohexane platinum compound, which like cisplatin, causes platinum-DNA adduct formation and destroys the integrity of DNA(23). Other types of chemotherapeutic agents, such as 5-FU, CPT-11, are common chemotherapeutic agents used in the treatment of colorectal cancer. Unfortunately, severe diarrhea has been identified as one of the dose-limiting toxicities among patients treated with chemotherapy.

Our studies showed that PHY906, an herbal composition, not only reduced chemotherapy-induced toxicities, including body weight loss and mortality, but it also enhanced the antitumor efficacy of a broad-spectrum of anticancer agents including, but not limited to CPT-11, 5-FU, CPT-11/5-FU/LV, VP-16, L-OddC and oxaliplatin/5-FU/LV in colorectal cancer; sorafenib, capecitabine, thalidomide, and CPT-11 in liver cancer; and capecitabine, oxaliplatin, gemcitabine and gemcitabine/oxaliplatin in pancreatic cancer in vivo animal models. The positive results from these preclinical studies demonstrate that PHY906 can be used as an adjuvant for a broad-spectrum of different types of chemotherapeutic agents in anti-cancer therapy. These chemotherapeutic agents include, but are not limit to, capecitabine and sorafenib. The cancers include, but are not limited to, colorectal, liver, and pancreatic cancers. The methods of the present invention can be used to improve the quality of life of patients including mammals under chemotherapy. Specifically, this invention relates to the dosing and scheduling of PHY906 in potentiating the therapeutic index of a broad-spectrum of cancer chemotherapeutic agents by the herbal composition PHY906.

The herbal compositions of the present invention are particularly useful with cancer chemotherapies, such as, but not limited to, treatment with irinotecan (CPT-11, Camptosar®), 5-fluorouracil (FU or 5-FU), leucovorin (LV), VP-16, beta-L-Dioxolane-cytidine (L-OddC), capecitabine, gemcitabine, oxaliplatin, doxorubicin, thalidomide, and combinations thereof, such as but not limited to FU/LV, CPT-11/FU/LV, oxaliplatin/FU/LV, and gemcitabine/oxaliplatin. The present invention provides compositions comprising PRY and one or more chemotherapeutic agents such as but not limited to CPT-11, 5-FU, VP-16, L-OddC, capecitabine, gemcitabine, oxaliplatin, and combinations thereof, such as but not limited to FU/LV, CPT-11/FU/LV, and oxaliplatin/FU/LV. The present invention also provides compositions comprising PHY906 and one or more analogs and derivatives of chemotherapeutic agents, such as CPT-11, 5-FU, VP-16, L-OddC, LV, capecitabine, gemcitabine, doxorubicin, thalidomide, and oxaliplatin.

In one embodiment, the present invention provides a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the plant species comprise *Scutellaria baicalensis, Glycyrrhiza uralensis, Ziziphus jujuba*, and *Paeonia lactiflora*. In another embodiment of the invention one or more chemotherapeutic compounds are cancer chemotherapeutics. In one embodiment of the invention the cancer chemotherapeutics are selected from the group consisting of capecitabine, sorafenib, and a combination thereof.

In one embodiment of the invention, a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is used to treat a disease in a mammal in need thereof. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the present invention provides a method of treating a disease in a mammal. The method comprises administering to the mammal in need thereof a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the present invention provides a method of relieving the side effects of a chemotherapeutic compound in a mammal. The method comprises administering to the mammal in need thereof a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to enhance the therapeutic effectiveness of chemotherapeutic compound. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to enhance the antitumor activity of a chemotherapeutic compound. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment it of the invention, a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to treat tumors. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to inhibit the growth of tumors in mammals. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is used to inhibit the growth of tumors. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*. In one embodiment, the tumors are present in a mammal or in vitro cells.

In one embodiment, the present invention provides a method of improving the quality of mammal undergoing chemotherapy. The method comprises administering a therapeutically effective amount of one or more chemotherapeutic compounds and a composition comprising: i) a pharmaceutically acceptable carrier; ii) materials or chemicals from a plant species of each of the following genera of herbs: *Scutellaria, Glycyrrhiza, Ziziphus* and *Paeonia;* and iii) one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*. Preferably, the mammal as referenced herein is a human.

The above-referenced chemotherapeutic agents or compounds, genera of herbs, and other terms and phrases have been described and defined with details in the following patent applications and patent: U.S. patent application Ser. No. 09/522,055 filed Mar. 9, 2000; international Application No. PCT/US2001/007353 filed Mar. 8, 2001; U.S. patent application Ser. No. 10/220,876 filed Dec. 30, 2002 and issued as U.S. Pat. No. 7,025,993 on Apr. 11, 2006; U.S. Provisional Patent Application Ser. No. 60/625,943 filed Nov. 9, 2004; U.S. patent application Ser. No. 11/100,433 filed Apr. 7, 2005; and International Application No, PCT/US2005/040605 filed Nov. 9, 2005, the content of which are herein incorporated by reference in their entirety for all purposes.

Pharmaceutical Formulations

The compositions of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, the type of concurrent treatment, if any, the frequency of treatment, and the nature of the effect desired.

The pharmaceutical formulation for systemic administration according to the invention may be formulated for enteral, parenteral, or topical administration. Indeed, all three types of formulations may be used simultaneously to achieve systemic administration of the active ingredient.

The present invention further provides compositions containing one or more agents which treat various types of cancer and/or modulate hematopoietic activity, such as the immunodulation of tuberculosis (T.B.), natural killer cells (NK), monocytes, and dendritic cells.

While individual needs vary, determination of optimal ranges of effective amounts of each component is within the skill of the art.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

PHY906 can be used in the form of a medicinal preparation, for example, in solid, semi-solid or liquid form which contains PHY906, as an active ingredient, in admixture with an organic or inorganic carrier or excipient suitable for external, enteral, or parenteral applications. The active ingredient may be compounded, for example, with the usual non-toxic pharmaceutically acceptable carriers for tablets, pellets, capsules, suppositories, solutions, emulsions, suspensions, and any other form suitable for use. Formulations of the present invention encompass those which include talc, water, glucose, lactose, gum acacia, gelatin, mannitol, starch paste, magnesium trisilicate, corn starch, keratin, colloidal silica, potato starch, urea, and other carriers suitable for use in manufacturing preparations, in solid, semisolid or liquid form and in addition auxiliary, stabilizing, thickening and coloring agents, and perfumes may be used.

For preparing solid compositions such as tablets or capsules, PHY906 is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of PHY906, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage firms such as tablets, pills and capsules. This solid preformulation composition is then subdivided into unit dosage forms of the type described above containing an effective amount of the composition of the present invention, preferably in capsules.

The tablets or pills containing PHY906 can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol, and cellulose acetate.

The liquid forms, in which PHY906 may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the compositions of the present invention may take the form of tablets or lozenges formulated in conventional manners. PHY906 may also be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

In practicing the methods of this invention, PHY906 may be used alone or in combination, or in combination with other therapeutic or diagnostic agents. In certain preferred embodiments, the compounds of this invention may be coadministered along with other compounds typically prescribed for cancer chemotherapy according to generally accepted medical practice. The compounds of this invention can be utilized in vivo, ordinarily in mammals, such as humans, sheep, horses, cattle, pigs, dogs, cats, rats and mice, or in vitro.

Actual methods for preparing administrable compositions and adjustments necessary for administration to subjects will be known or apparent to those skilled in the art and are described in more detail in, for example, Remington's Pharmaceutical Science, 17th Ed., Mack Publishing Company, Easton, Pa. (1985), which is incorporated herein by reference.

Methods of Using PHY906

The present invention provides methods of using PHY906 in combination with therapeutics for the treatment of various diseases, conditions, or disorders.

Specifically, the present invention provides methods of using PHY906 in combination with chemotherapeutic agents for the treatment of diseases, conditions, or disorders. Preferably, the present invention provides a method of treating cancer comprising administering one or more cancer chemotherapeutic agents in combination with PHY906 to a patient. The chemotherapeutic agents include but are not limited to CPT-11, 5-FU/LV, VP-16, L-OddC, capecitabine, gemcitabine, oxaliplatin, thalidomide, doxorubicin, and combinations thereof. More preferably, the present invention provides a method of treating colorectal cancer, pancreatic cancer, hepatocellular carcinoma comprising administering CPT-11/FU/LV oxaliplatin/FU/LV, or oxaliplatin/gemcitabine in combination with PHY906.

The present invention contemplates methods of using PHY906 in combination with antiviral agents for the treatment of diseases, conditions, or disorders. Preferably, the present invention provides a method of treating a disease associated with a viral infection comprising administering one or more antiviral agents in combination with PHY906 to a patient. More preferably, the present invention provides a method of treating AIDS comprising administering one or more anti-retroviral drugs in combination with PHY906. Even more preferably, the anti-retroviral drug is selected from the group consisting of AZT, D4T, DDC, 3TC, and DDI. Most preferably, a combination comprising three antiviral drugs and PHY906 is administered to the patient. The preferred combination of three antiviral drugs include, but are not limited to, 1) D4T, 3TC, and protease inhibitor; 2) AZT, 3TC, and protease inhibitor; and 3) AZT, DDI, and protease inhibitor. The preferred protease inhibitor for treating HIV include, but not limited to, nelfinavir, indinavir, saquinavir, and ritonavir.

in one aspect of the invention, PHY906 is administered to cell lines, for example cancer or carcinoma cell lines and HIV cell lines, to evaluate the toxicity of PHY906 on different cell lines. Preferably, the cancer or carcinoma cell lines include, but are not limited to Jurkat, KB, HepG2, Hep (11.6, T-cell lymphoma (CEM), Colon 26, Colon 38, HCT116, PANC 01, PANC 02, HPAC, and the HIV cell lines include, but are not limited to, H9 cells and MT-2 cells.

In another aspect of the invention, PHY906 in combination with one or more chemotherapeutic or antiviral agent is administered to an animal to determine whether PHY906 is effective in increasing the therapeutic index of the agent and the quality of life of the animal undergoing chemotherapeutic or antiviral therapy. Preferably, the animal is a mammal. More preferably, the mammal is a human.

The animal could be an animal model for a specific cancer or viral disease. Also, the animal could have a deficient immune system. Such animal models are well-known in the art. Naturally-occurring immunodeficient mice have been used to study the immune system, cancer, and infectious diseases, including acquired immune deficiency syndrome or AIDS. For example, the nude (NU) mouse is athymic, so T cell differentiation and maturation cannot occur. Nude mice have served for many years as host for xenografts, especially human tumors and the testing of anti-cancer drugs. The severe combined immunodeficiency syndrome (SCID) mouse appears to defectively rearrange both TCR (T cell receptor) and immunoglobulin genes and displays a severe immunodeficiency. The beige (BG) mouse carries a defect in functional natural killer cells, whereas the X-linked immunodeficient (XID) mouse has a defect in the production of B cells. In addition, crosses have been made among various strains to generate lines with more comprehensive immunodeficient pheno-types BG/NU and BG/NU/XID).

Other laboratory animals which possess little or no immune system of their own, or which have been treated with drugs or radiation, or produced through traditional genetic development or genetic engineering to have either a suppressed immune system, a weakened immune system or a modified immune system, or no immune system at all, such as, e.g. SCID horses and other SCID animals and potentially even AIDS infected animals in which AIDS has been arrested after destruction or inactivation of the animals' immune system may be considered as laboratory animal candidates for use in the present invention (Perryman L. E., McGuire, T. C., Torbeck, R. L., and Magnuson, N. S., Clin. Immunol. Immunopath., 23(1):1-9, 1982).

Murine models to study transplacental or perinatal antiretroviral therapy are known (Sharpe et al. (1987) Science 236: 1671-1674; Sharpe et al. (1988) Proc. Natl. Acad. Sci. (USA) 85: 9792-9796; Sharpe et al. (1989) J. Virol. 63: 1049-1053). In addition, mammalian models utilizing rhesus monkeys have been established to study the course of non-retroviral fetal infection by simian cytomegalovirus, Venezuelan and Western equine encephalitis virus, and mumps virus (London et al. (1986) Teratology 33: 323-331; London et al. (1977) Teratology 16: 285-296; London et al. (1982) Teratology 25: 71-79; London et al. (1979) J. Inf. Diseases 139: 324-328). Infection of rhesus monkeys (*Macaca mulatta*) with simian immunodeficiency virus (SIV) closely mimics HIV-1 infection in humans. Both HIV-1 and SIV are lentiviruses with similar molecular architecture (Chakrabarti et al. (1987) Nature 328: 543-547), and both cause immunodeficiency resulting in opportunistic infections as well as central nervous system damage (Lavin et al. (1985) Science 230: 71-73).

An animal model generated to study AIDS and bone marrow cell differentiation has been reported in which human lymphocytes are transiently proliferated upon coengrafting human fetal liver, thymus, and lymph nodes into SCID mice to form a SCID/nu mouse (McCune et al. (1988) Science 241: 1632-1686). Human immune tissues in these mice are susceptible to human immunodeficiency virus (HIV) infection (Namikawa et al. (1988) Science 242: 1684-1686) and the model has recently been used to test the effectiveness of AZT in delaying the replication of the AIDS virus.

U.S. Pat. No. 6,184,436 discloses a transgenic mouse to serve as a small animal model of AIDS. The mouse comprises a transgene comprising a DNA sequence encoding HIV-1 in operable linkage with the human CD4 promoter flanked by the enhancer of the mouse CD4 gene. The mouse develops a severe AIDS disease and leads to an early death.

In a preferred embodiment, the animals treated with one or more chemotherapeutic or antiviral agents in combination with PHY906 are evaluated for weight loss and survival rate and compared to control animals which are only administered the one or more chemotherapeutic or antiviral agents. The effect of PHY906 on the antitumor or antiviral activity could also be evaluated to determine the efficacy of PHY906.

Specifically, PHY906 can be evaluated as a modulator of antiviral therapy, such as AIDS. Any of the animal models for AIDS described above can be used. The first step involves determining the maximum tolerable dose of antiviral agent or combination of antiviral agents to administer to healthy animals by evaluating the weight loss of the animals. The second step involves administering the antiviral agent or agents in combination with PHY906 to the animals diagnosed with AIDS. The weights of the animals are evaluated and compared to control animals that did not receive PHY906 over the course of the treatment. Also, the hematological toxicity of the combination of PHY906 and antiviral agent or agents are evaluated by determining the red blood cell count or platelet count. The white blood cell counts of the animals are evaluated to determine the effectiveness of the combination of PHY906 and antiviral agent or agents in treating the animal of AIDS. The results of each assay are compared to those of control animals that are not given PHY906.

Formulations for Combination Therapy

The present invention provides combination therapy comprising a composition containing one or more compounds and PHY906 for the treatment of cancer, specifically colorectal cancer, pancreatic cancer, and hepatocellular carcinoma. Preferably, the compounds are chemotherapeutic agents such as CPT-11, 5-FU, LV, VP-16, L-OddC, capecitabine, gemcitabine, thalidomide, doxorubicin, and oxaliplatin. The compounds could also be antiviral agents such as AZT, DDI, 3TC, and D4T. The combination therapy may administer the compounds together with PHY906 as a composition or administer the compounds separately from the administration of PHY906. Therapy may be performed with the composition of the present invention alone or in conjunction with another therapy (e.g., surgery, radiation, biologic therapy).

The administration dosage and frequency of each component of the composition can be controlled independently. For example, one component may be administered orally three times per day, while the second component may be administered intramuscularly once per day. The compounds and PHY906 may also be formulated together such that one administration delivers both components. Formulations and dosages are described below.

Formulation of Pharmaceutical Compositions: The administration of each chemotherapeutic agent and PHY906 of the composition may be by any suitable means that results in a concentration of the compound that, combined with the other component, is specifically anti-neoplastic upon reaching the target region. The chemotherapeutic agent may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalent, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988-1999, Marcel Dekker, New York.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination with PHY906, has (i) a narrow therapeutic index (i.e. the difference between the plasma concentration leading to harmful side effects or toxic reactions and the plasma concentration leading to a therapeutic effect is small; in general, the therapeutic index, TI, is defined as the ratio of median lethal dose (LD 50) to median effective dose (ED 50)); (ii) a narrow absorption window in the gastro-intestinal tract; or (iii) a very short biological half-life so that frequent dosing during a day is required in order to sustain the plasma level at a therapeutic level.

Any of a number of strategies can be applied in order to obtain a controlled release formulation in which the rate of release outweighs the rate of metabolism of the compound in question. In one example, controlled release is obtained by appropriate selection of various formulation parameters and ingredients, including, e.g., various types of controlled release compositions and coatings. Thus, the drug substance is formulated with appropriate excipients into a pharmaceutical composition that, upon administration to the organism, releases the active substance in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use: Formulations of the composition comprising PHY906 and one or more compounds for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Alternatively, the compounds may be formulated for oral use separately from PHY906.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g. based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology, supra.

The compounds and PHY906 may be mixed together in the tablet, or may be partitioned. In one example, the first drug is contained on the inside of the tablet, and the second drug is on the outside, such that a substantial portion of the second drug is released prior to the release of the first drug.

Formulations for oral use may also be presented as chewing tablets, or as hard gelatin capsules wherein the active ingredient is mixed with an inert solid diluent (e.g., potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms: Controlled release compositions containing the compounds alone or in combination with PHY906 for oral use may, e.g., be constructed to release the active drug substance by controlling the dissolution and/or the diffusion of the active drug substance.

Dissolution or diffusion controlled release can be achieved by appropriate coating of a tablet, capsule, pellet, or granulate formulation of compounds, or by incorporating the compound in question into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylatemethyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time. A buoyant tablet formulation of the compound(s) can be prepared by granulating a mixture of the drug(s) with excipients and 20-75% w/w of hydrocolloids, such as hydroxyethylcellulose, hydroxypropylcellulose and hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration: The compounds alone or in combination with PHY906 may be formulated as liquids for oral administration. Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions: The pharmaceutical composition of the present application comprising the compounds alone or in combination with PHY906 may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions is well-known to those skilled in the art of pharmaceutical formulation. Specific formulations can be found in Remington: The Science and Practice of Pharmacy, supra.

Compositions for parenteral use may be presented in unit dosage forms e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The compounds may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions: Controlled release parenteral compositions may be in form of aqueous suspensions, microspheres, microcapsules, magnetic microspheres, oil solutions, oil suspensions, or emulsions. Alternatively, the compounds may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and, polylactic acid). Biocompatible carriers that may be used when formulating a controlled release parenteral formulation are carbohydrates (e.g., dextrans), proteins (e.g., albumin), lipoproteins, or antibodies.

Materials for use in implants can be non-biodegradable (e.g., polydimethyl siloxane) or biodegradable (e.g., poly (caprolactone), poly(lactic acid), poly(glycolic acid) or poly (ortho esters)).

Rectal Compositions: The compounds alone or in combination with PHY906 may be formulated for rectal administration. For rectal application, suitable dosage firms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

Compositions for Inhalation: The compounds alone or in combination with PHY906 may be formulated for inhalation. For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions: The compounds alone or in combination with PHY906 may be formulated for percutaneous and topical administration. The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and Azone™ Examples of chelating agents are sodium EDTA, citric acid, and phosphoric acid. Examples of gel forming agents are Carbopol™, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (Tween)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions: The compounds alone or in combination with PHY906 may be formulated for controlled release percutaneous and topical administration. There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be Obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a non-porous polymeric membrane (e.g., ethylene-vinyl acetate copolymer). The active compound is only permitted to be released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages: The dosage of each compound depends on several factors, including: the administration method, the disease to be treated, the severity of the disease, whether the disease is to be treated or prevented, and the age, weight, and health of the person to be treated.

The compounds are preferably administered in an amount of about 0.1-30 mg/kg body weight per day, and more preferably in an amount of about 0.5-15 mg/kg body weight per day. As described above, the compound in question may be administered orally in the form of tablets, capsules, elixirs or syrups, or rectally in the form of suppositories. Parenteral administration of a compound is suitably performed in the form of saline solutions or with the compound incorporated into liposomes. In cases where the compound in itself is not sufficiently soluble to be dissolved, a solubilizer such as ethanol can be applied.

EXAMPLES

Example 1

Materials and Methods

Drug: Sorafenib (Nexavar) was purchased from Bayer HealthCare (Leverkusen, Germany). Capecitabine (Xeloda®, CAP) was purchased from Roche Laboratories Inc. (Nutley, N.J.). The clinical drug substance of PHY906 (PHY906-6, FDA 165542) with 10% excipient was prepared by Sun Ten Pharmaceutical, Inc. (Taipei, Taiwan). The PHY906 formula is composed of four herbs: *Scutellariae baicalensis* Georgi, *Paeonia lactiflora*. Pall., *Ziziphus jujuba*. Mill and *Glycyrrhiza uralensis* Fisch., with a relative weight ratio of 3:2:2:2.

Mice: Female BDF-1 mice with body weights between 16 and 20 g (4-6 weeks old) were purchased from Charles River Laboratories (Wilmington, Mass.). Male NCr athymic nude mice with body weights between 16 and 20 g (4-6 weeks old) were purchased from Taconic Farms (Garmantown, N.Y.).

Preparation of Sorafenib solution: Sorafenib (200 mg/tablet) was dissolved in 5% gum arabic as the vehicle. The final solution contains 30 mg/ml of sorafenib.

Preparation of capecitabine solution from capecitabine tablet: Capecitabine (150 mg/tablet) was dissolved in 40 mM citrate buffer (pH 6.0) containing 5% gum arabic as the vehicle. The final solution contains 36 mg/ml of capecitabine.

Preparation of herbal extract from dry powder: The preparation of the herbal extract followed SOP#HERB-001-PHY906. Briefly, one gram of PHY906 dry powder, containing 10% starch excipient, was added to 10 ml of 80° C. $H_2O$ and incubated at 80° C. for 30 minutes. The supernatant was separated from the debris by centrifugation (12000 rpm, 10 min) at room temperature. The concentration of PHY906 supernatant was calculated as 90 mg/ml of PHY906 (1 g/10 ml×0.9), based on the dry weight of the dry powder. The herbal extract was stored at room temperature and used within 24 hours. Any residual precipitant that occurred upon standing was vortexed into a suspension and used to treat the animals.

Tumor cells: The human hepatocellular carcinoma HepG2, human PANC-1 pancreatic cancer, and mouse Colon 38 colorectal cancer cell lines were purchased from the American Type Culture Collection (Rockville, Md.). The HepG2 and Colon 38 cell lines were routinely grown in MEME media while the PANC-1 cell line was grown in DMEM media, supplemented with 10% fetal bovine serum (FBS). The cells were implanted into the left flank of mice. Tumor transplantation from mice to mice was performed when the tumor reached 1500-2000 $mm^3$.

Mouse tumor model: Tumor cells ($5 \times 10^6$ cells in 0.1 ml PBS) were transplanted subcutaneously into the left flank of mice. After 14 days, tumor ranging in size from 300-500 $mm^3$ was selected for drug studies. The length and width of the each tumor was measured with sliding calipers. The tumor size was estimated according to the following formula:

$$\text{Tumor size (mm}^3) = \text{length (mm)} \times \text{width (mm)}^2/2.$$

The studies were conducted and the animals were maintained at the Yale Animal Facility.

Antitumor activity of chemotherapeutic agents in the presence or absence of PHY906: A total of 20 tumor-bearing mice were divided into 4 groups (N=5 mice/group):
1. Vehicle
2. PHY906
3. Chemotherapeutic agent
4. PHY906+Chemotherapeutic agent The first day of drug treatment was defined as day 1. PHY906 (500 mg/kg, bid) was administrated orally to the mice 30 min before chemotherapeutic agents at the days indicated. Chemotherapeutic agents were given either intraperitoneally or orally at the dose and schedule indicated. The tumor size, body weight, and mortality of the mice were monitored daily. Mice were sacrificed when the tumor size reached 10% of body weight.

Immunohistochemistry: Formalin-fixed paraffin-embedded liver tissue was freshly cut into slices of 4 mm. The sections were mounted on Superfrost slides, dewaxed with xylem, and gradually hydrated. Antigen retrieval was achieved by 0.05% citraconic anhydride buffer (pH 7.4) at 94° C. for 1 h. The primary HIF-1α, CD31 or VEGF antibodies was diluted 1:75 using Tris-HCl buffer containing 1% BSA and 0.5% Tween-20. The primary antibody was incubated at room temperature for 1 hour. As a negative control, two slides were processed without primary antibody. Detection took place by the conventional labeled streptavidin-biotin method with alkaline phosphatase as the reporting enzyme according to the manufacturer's instructions. DAB (3,3'-diaminobenzidine tetrahydrochloride, purchased from Sigma-Aldrich, St Louis, Mo.) served as chromogen. Afterwards, the slides were briefly counterstained with hematoxylin and aqueously mounted.

Statistical analysis and statistical power of the study (24): A random effects model was employed to analyze data from similar dosing animal trials. The PROC MIXED procedure in SAS was used to take into account the correlation among observations collected from the same mouse.

The following model was used to analyze the longitudinal data:

$$y_{ijk} = \mu + \alpha t_k + \beta(I_D t_k) + \gamma(I_P t_k) + \delta(I_D I_P t_k) + e_{ijk},$$

where $y_{ijk}$ is the relative tumor size of the jth individual with the ith group (no treatment, drug alone, PHY906 alone, and drug+PHY906) at the kth time point, $t_k$ is the kth time point, $\alpha$ is the baseline time effect (no treatment group), $I_D$ and $I_P$ are indicator variables for having the drug treatment and the PHY906 treatment, $\beta$ is the drug-specific linear time effect, $\gamma$ is the PHY906-specific linear time effect, $\delta$ is the drug-PHY906 synergistic linear time effect, and $e_{ijk}$ is the residual (error) term. We assumed that the errors from different individuals are independent, and errors from the same individual at different time points follow the autoregressive model, AR(1), to take into account the fact the observations from the same individual within the same treatment group are more correlated, and the responses from closer time points are more correlated within the same individual. The PROC MIXED in SAS 8.01 was used to perform the statistical analysis.

Results
(1) Sorafenib
Effect of PHY906 in Antitumor Activity of Sorafenib in Murine Colon 38 Bearing BDF-1 Mice To determine whether the combinational use of PHY906 and sorafenib in order to improve anti-tumor activity of sorafenib. Sorafenib at dose of 30 mg/kg (BID, D1-14), in combination with a fixed dose of PHY906 at 500 mg/kg (BID, D1-4 and 8-11), were studied in BDF-1 mice bearing Colon 38 murine colorectal cancer. As shown in FIG. 1, PHY906 significantly enhanced the antitumor activity of sorafenib in Colon 38 bearing mice. Indeed, the tumor growth was suppressed when mice received the combination of PHY906 and sorafenib.

Figure 2:
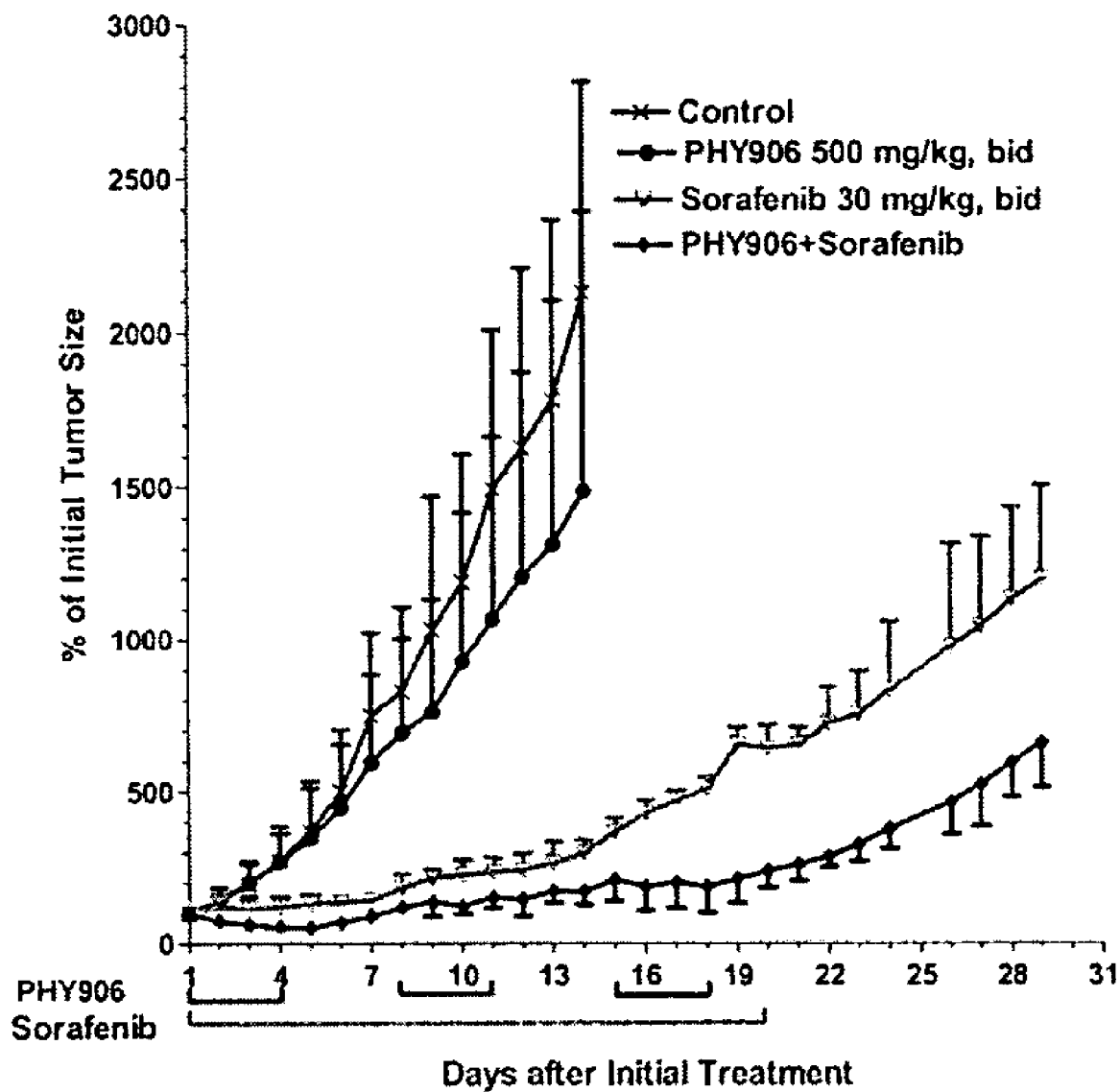
FIG. 2 shows the effect of PHY906 (500 mg/kg, bid, D1-4, 8-11 and 15-18) on tumor growth in Sorafenib (30 mg/kg, po, bid, D1-20)-treated nude mice bearing human HepG2 tumors. Sorafenib (30 mg/kg) was given orally twice a day for a consecutive 20 days. PHY906 (500 mg/kg) was given orally 30 min before sorafenib twice a day on days 1-4, 8-11 and 15-18 (N=5 in each group).

Effect of PHY906 in Antitumor Activity, (b) Blood Vessels, (c) VEGF Level and (d) HIF-1α of Sorafenib in Human HepG2 Xenografts PHY906 (500 mg/kg, BID, D1-4, 8-11 and 15-18) was tested on the antitumor activity of sorafenib 130 mg/kg, BID, D1-20) in human HepG2 bearing nude mice. As shown in FIG. 2, the combination of sorafenib and PHY906 shrank the tumor size approximately 60% after the first week of combination drug treatment while mice treated with sorafenib alone did not have the shrinkage in tumor.

Figure 3:
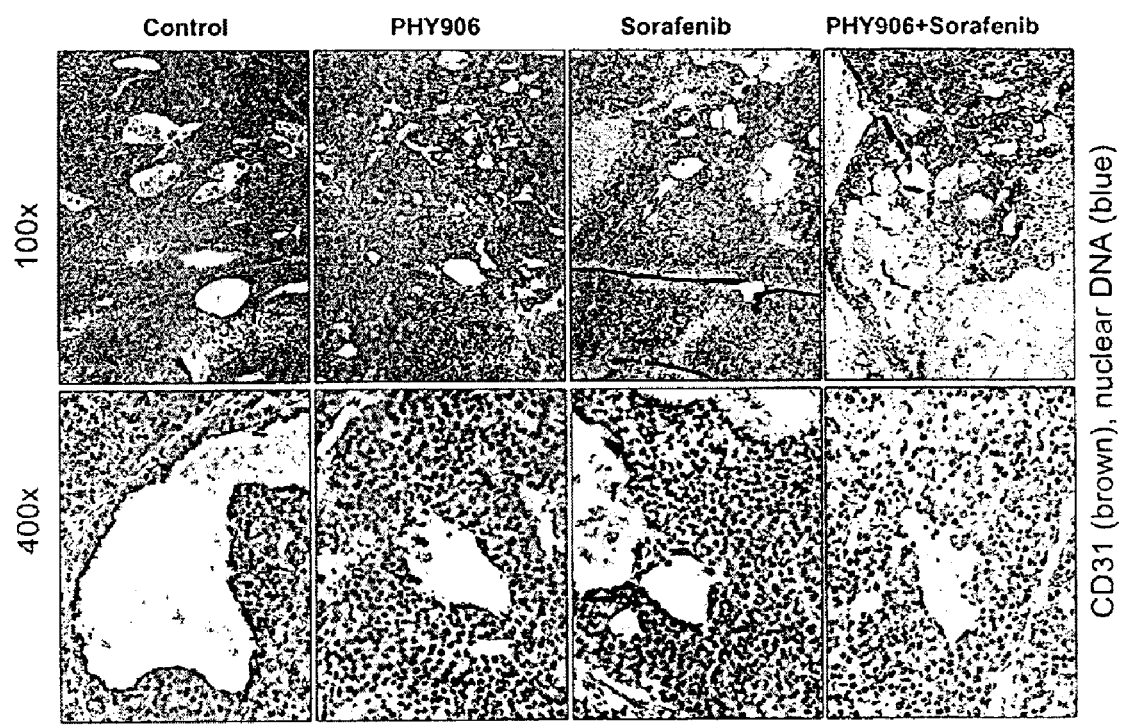
FIG. 3 shows the impact of PHY906 and Sorafenib on blood vessels from the liver of NCr-nude mice bearing human HepG2 xenografts. Tissue sections were prepared from formalin-fixed, paraffin-embedded liver cancer specimens. Immunohistochemical staining was done using specific antibodies against CD31 (brown) and nuclear DNA (blue).
Figure 4:
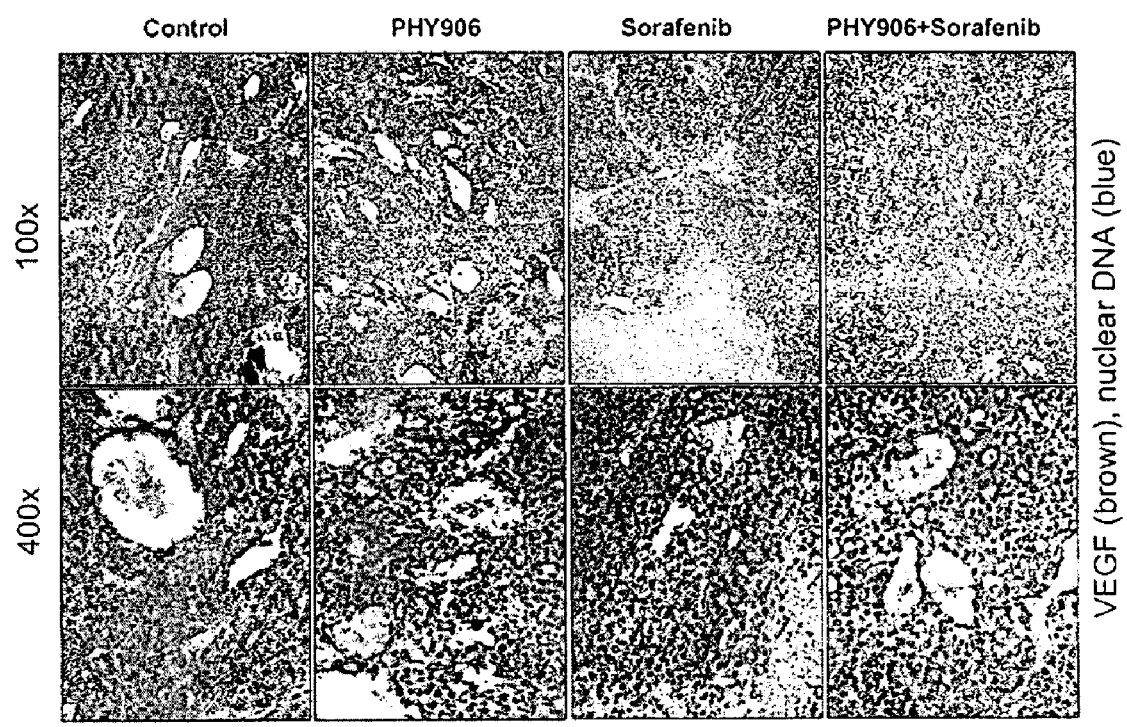
FIG. 4 shows impact of PHY906 and Sorafenib on VEGF level from the liver of NCr-nude mice bearing human HepG2 xenografts. Tissue sections were prepared from formalin-fixed, paraffin-embedded liver cancer specimens. Immunohistochemical staining was done using specific, antibodies against VEGF (brown) and nuclear DNA (blue)
Figure 5:
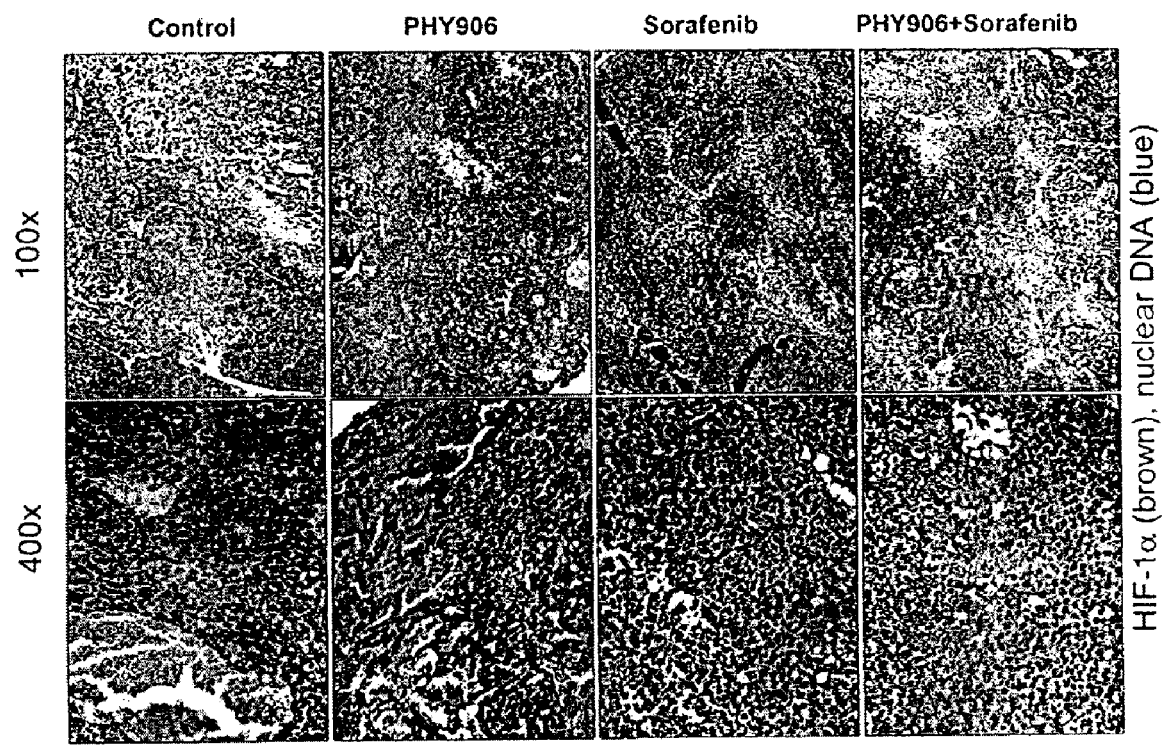
FIG. 5 shows the impact of PHY906 and Sorafenib on HIF-1α level from the liver of NCr-nude mice bearing human HepG2 xenografts. Tissue sections were prepared from formalin-fixed, paraffin-embedded liver cancer specimens. Immunohistochemical staining was done using specific antibodies against HIF-1α (brown) and nuclear DNA (blue).

The immunohistochemical stainings on mouse liver indicate that the integrity of tumor blood vessels are destroyed with the combination treatment of PHY906 and sorafenib, as shown in FIG. 3. The expressions of VEGF and HIF-1α are suppressed by the combination treatment of PHY906 and sorafenib, as shown in FIGS. 4 and 5, respectively. The data also suggests that the combination treatment of PHY906 and sorafenib affects the Fos/Juk transcription.

Figure 6:
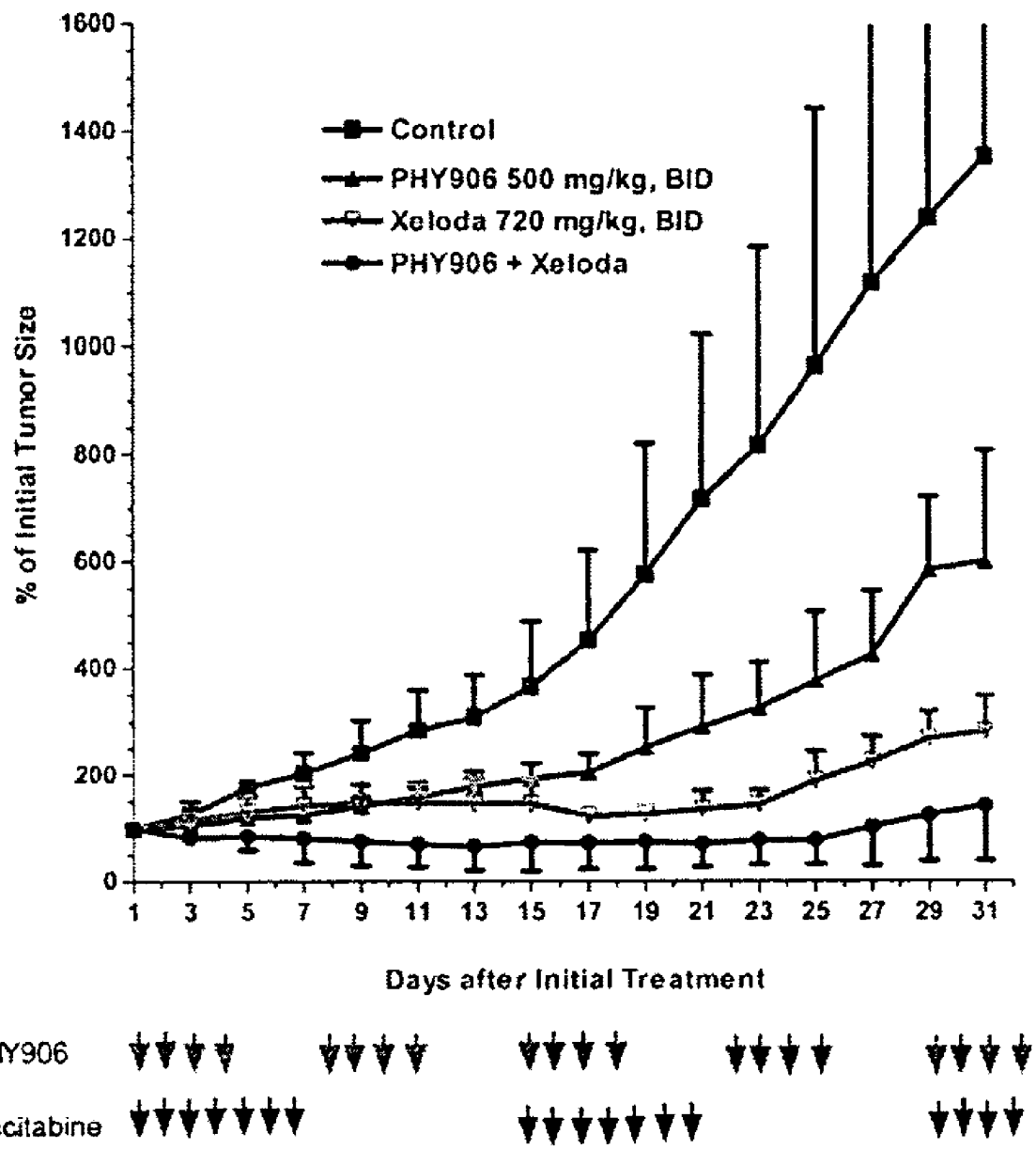
FIG. 6 shows the effect of PHY906 on the tumor growth in Capecitabine-treated NCr-nude mice bearing human Panc-1 tumor. Capecitabine (720 mg/kg) was given orally twice a day on days 1-7, 15-21 and 29-32 days. PHY906 was given orally 30 min before capecitabine twice a day on days 1-4, 8-11, 15-18, 22-25 and 29-32 at 500 mg/kg (=5 in each group)

(2) Capecitabine
Effect of PHY906 on the Antitumor Activity of Capecitabine in Human Panc-1 Tumor-Bearing Nude Mice PHY906 was previously found to potentiate the antitumor activity of capecitabine in human HepG2 xenografts. An experiment was therefore conducted to study whether PHY906 could enhance the antitumor activity of capecitabine in human Panc-1 xenografts. Total 20 NCr nude mice transplanted with Panc-1 human pancreatic carcinoma cells were divided into 4 groups (N=5 mice/group): Group (A) vehicle control; Group (B) treated with PHY906 (500 mg/kg, bid, day 1-4, 8-11, 15-18, 22-25 and 29-32); Group (C) treated with capecitabine (720 mg/kg, bid, day 1-7, 15-21, and 29-32); and Group (D) treated with PHY906 (500 mg/kg, bid, days day 1-4, 8-11, 15-18, 22-25 and 29-32) plus capecitabine (720 mg/kg, bid, day 1-7, 15-21, and 29-32). PHY906 was found to enhance the antitumor activity of capecitabine, as shown in FIG. 6. A similar observation was found with lower doses of capecitabine (data not shown).

Example 2

Effect of PHY906 on the Antitumor Activity of FU/LV in BDF-1 Mice Bearing Colon 38 Tumors FU/LV in combination shows potent antitumor activity and is used as the firstline treatment of colorectal cancer in patients (Goldber R. M. and Erlichman C., Oncology 12: 59-63 (1988); Saitz L. B, Cox J. V, Blanke C, et al., New. Eng. J. Med. 343:905-914 (2000)). Therefore, experiments similar to that described above for CPT-11 treatment were carried out with FU/LV in animals. Colon 38 tumor bearing mice were divided into four groups: Group (A) treatment with vehicle; Group (B): treatment with PHY906 alone; Group (C) treatment with FU/LV alone; and Group (D) treatment with FU/LV plus PHY906. The sequence of each regimen appears in Materials and Methods. In this set of experiments, FU/LV was given to mice only once on day 0, whereas PHY906 was administered twice daily for 4 consecutive days.

Figure 7:
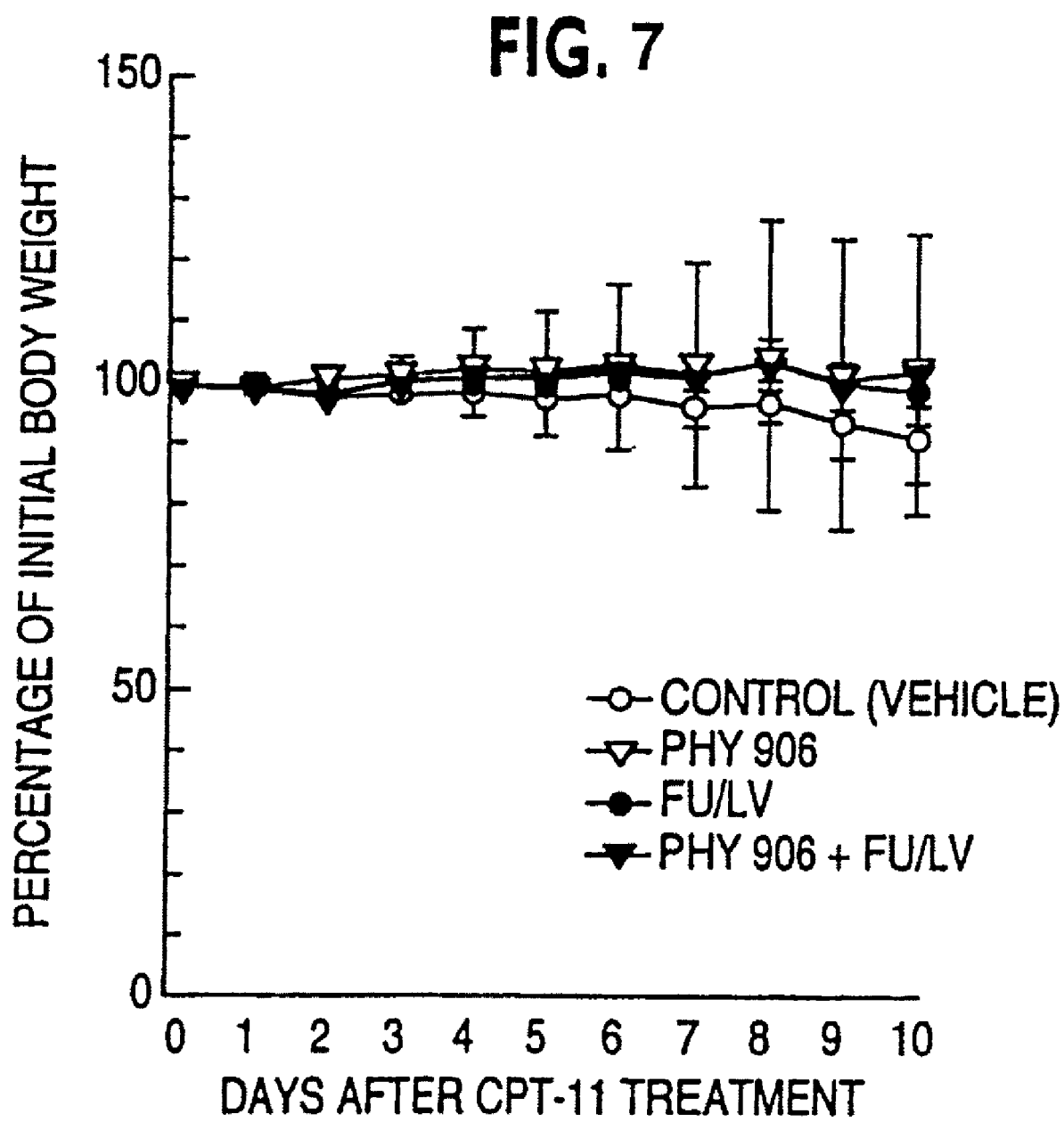
FIG. 7. Effect of PHY906 on Body Weight in FU/UV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 8:
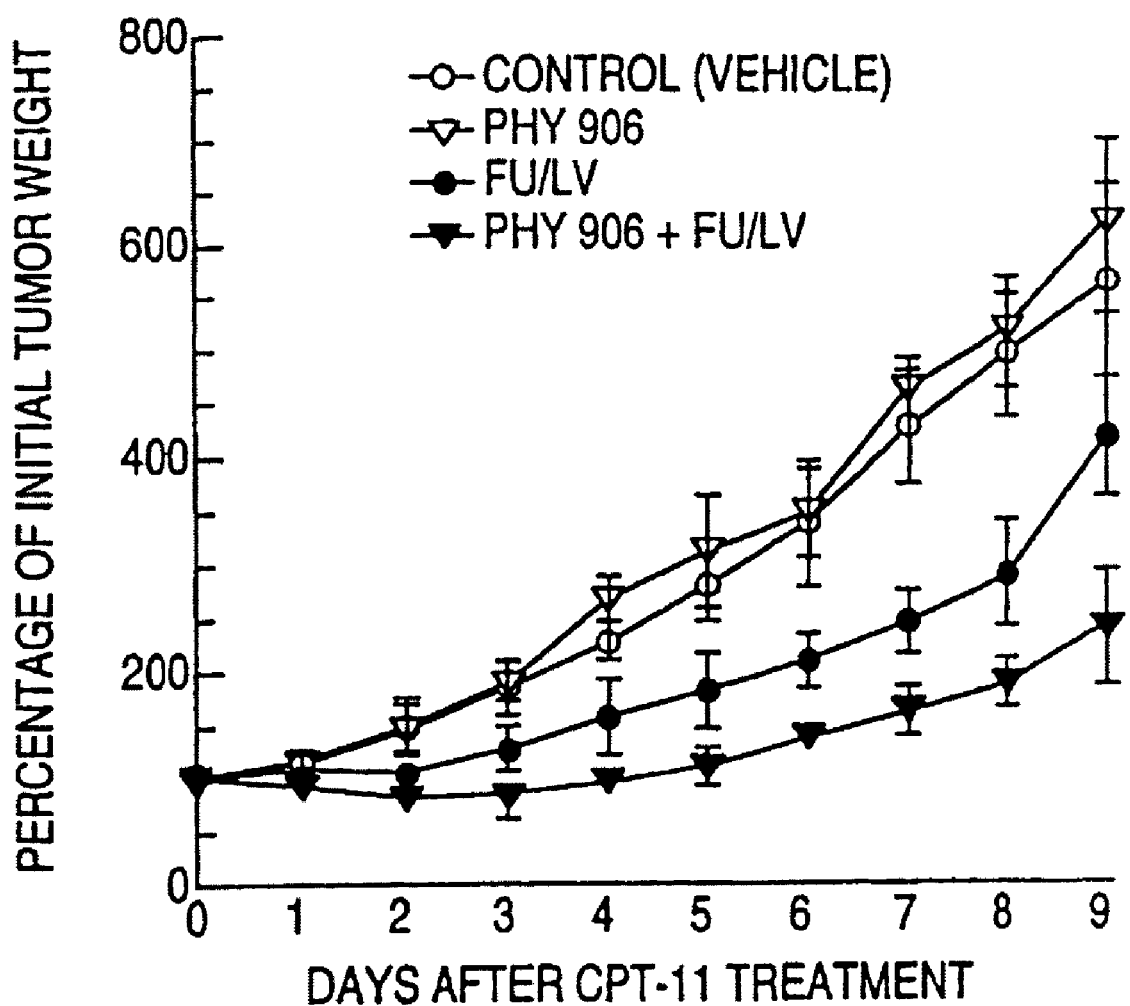
FIG. 8. Effect of PHY906 on Tumor Growth in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 9:
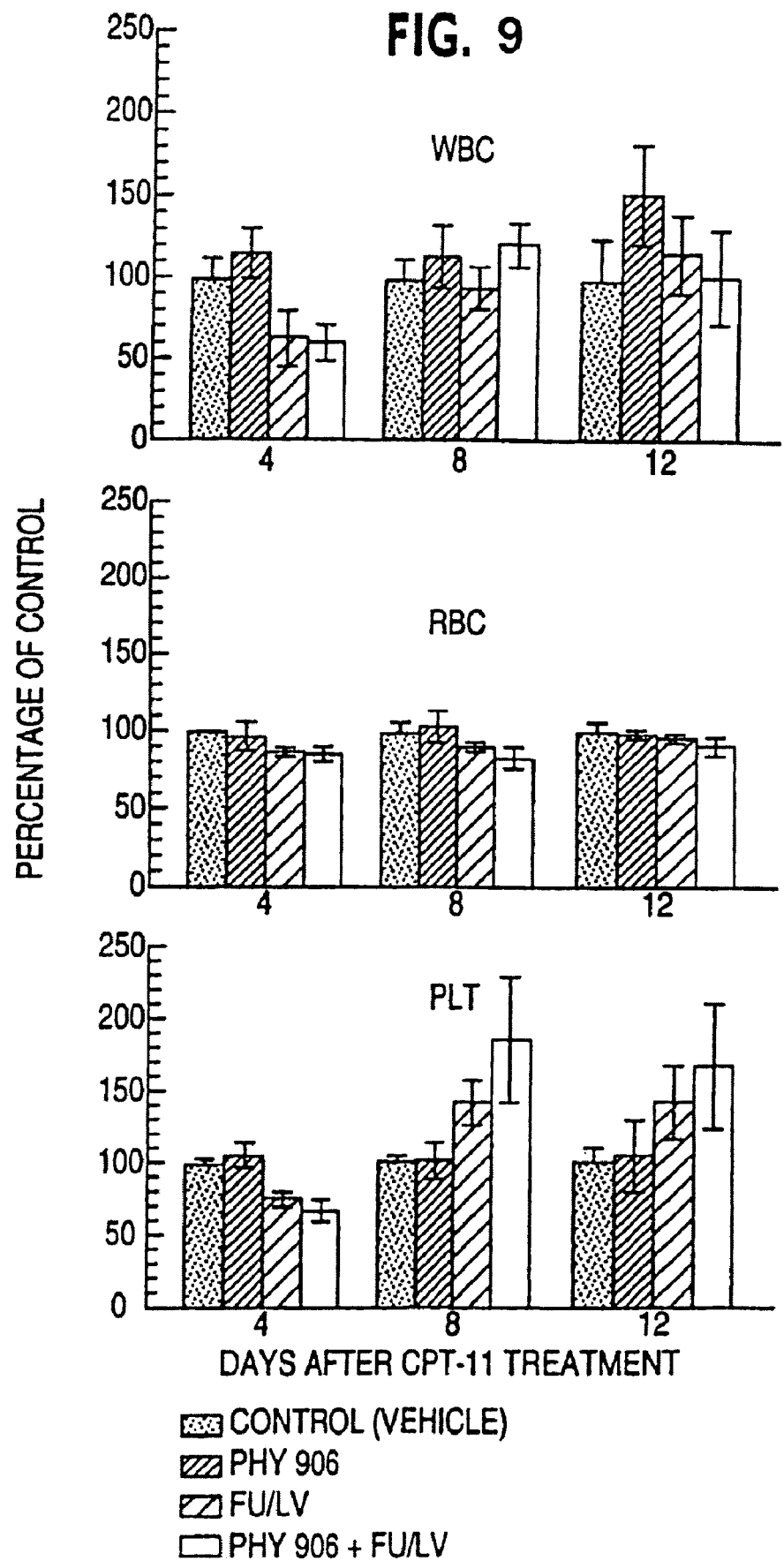
FIG. 9. Effect of PHY906 on Hematological Change in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Changes in body weight and tumor size were monitored daily, as shown in FIGS. 7 and 8, respectively. As depicted in FIG. 7, little change in body weight occurred in the four groups. This observation is in contrast to that obtained with CPT-11 treatment. Since dose-response studies of FU/LV on body weight loss were not performed, it is possible that the FU/LV dose administered in this experiment was not high enough to induce toxicity and associated body weight loss. Although body weight loss was insufficient to demonstrate a protective effect PHY906 on FU/LV, FIG. 8 indicates that concomitant treatment of PHY906 did not impair the antitumor activity of FU/LV in BID-1 mice bearing Colon 38 tumors. The tumor growth profile of animals in Group D is slower than that in Group C, suggesting that PHY906 may enhance the antitumor activity of FU/LV in this animal model. In addition, the hematological toxicity of FU/LV in treated mice concomitantly administered PHY906 was monitored on days 4, 8, and 12. Leucopenia or thrombocytopenia, well known side effects induced by FU/LV (van der Wilt C. L, van Groeningen, C. J, Pinedo H. M, et al., J. Cancer Res. Clin. Oncol. 123:595-601 (1997)), was not reversed by PHY906 (FIG. 9).

Example 3

Pharmacokinetics of CPT-11/FU/LV in BDF-1 Mice Bearing Colon 38 Tumor in the Presence and Absence of PHY906

Figure 10:
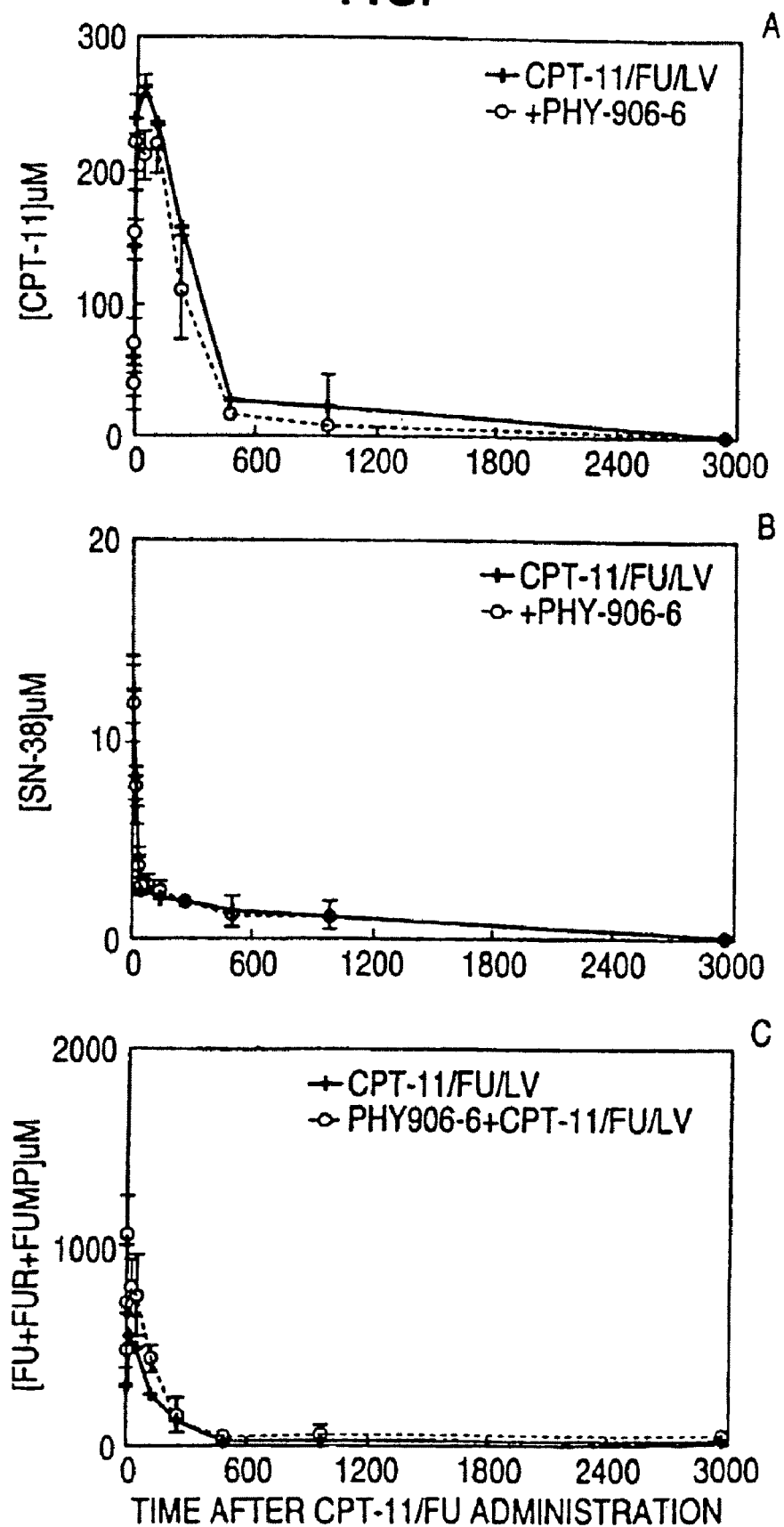
FIG. 10 A-C. Pharmacokinetic of CPT-11/FU/LV in Plasma. PHY906-6 is the clinical batch of PHY906. SN-3$ is an active metabolite of CPT-11. FUR+FUMP are nucleoside and nucleotide metabolites of FU.
Figure 11:
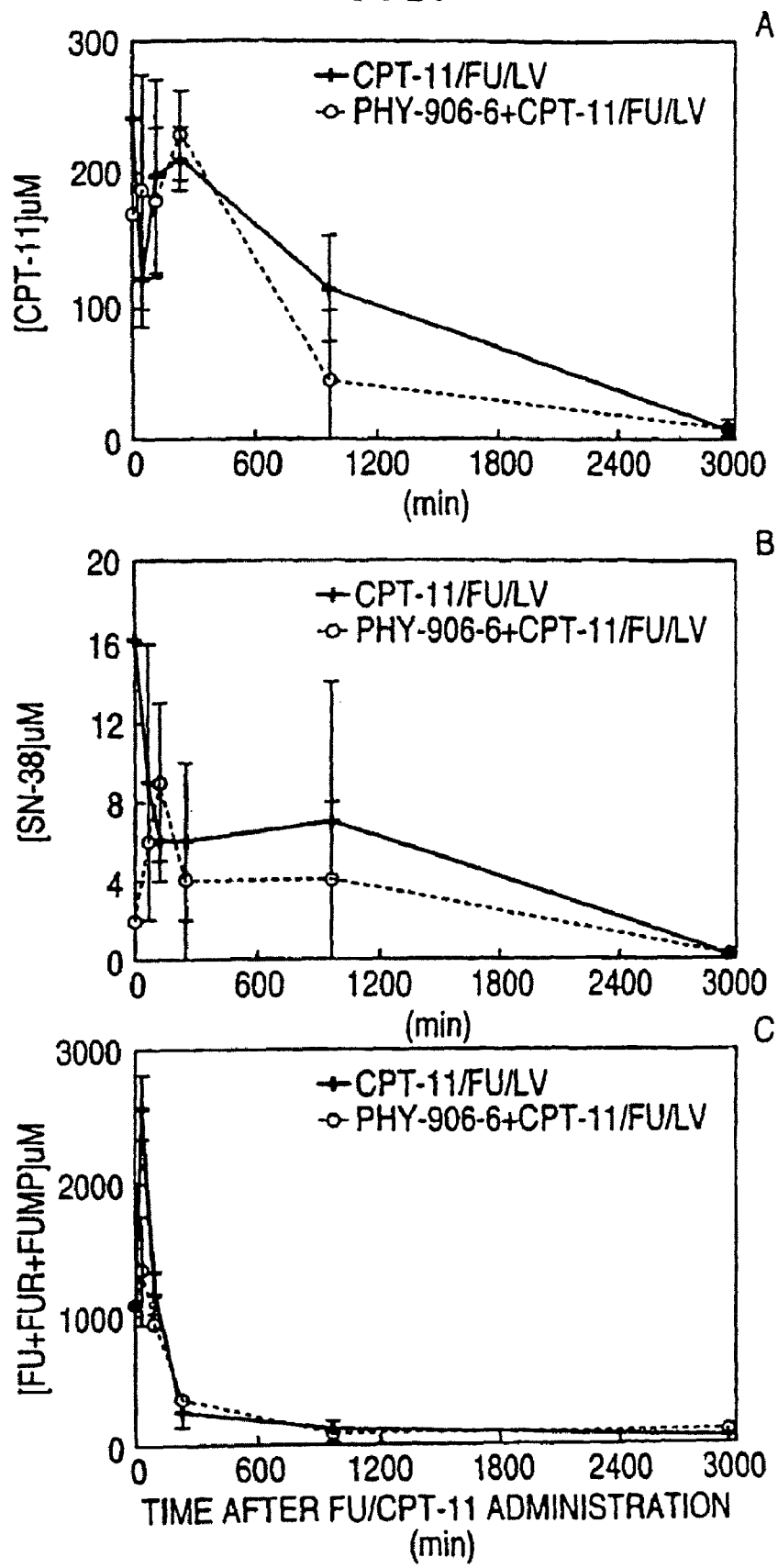
FIG. 11 A-C. Pharmacokinetic of CPT-11/FU/LV in Liver. PHY906-6 is the clinical batch of PHY906. SN-38 is an active metabolite of CPT-11. FUR+FUMP are nucleoside and nucleotide metabolites of FU.
Figure 12:
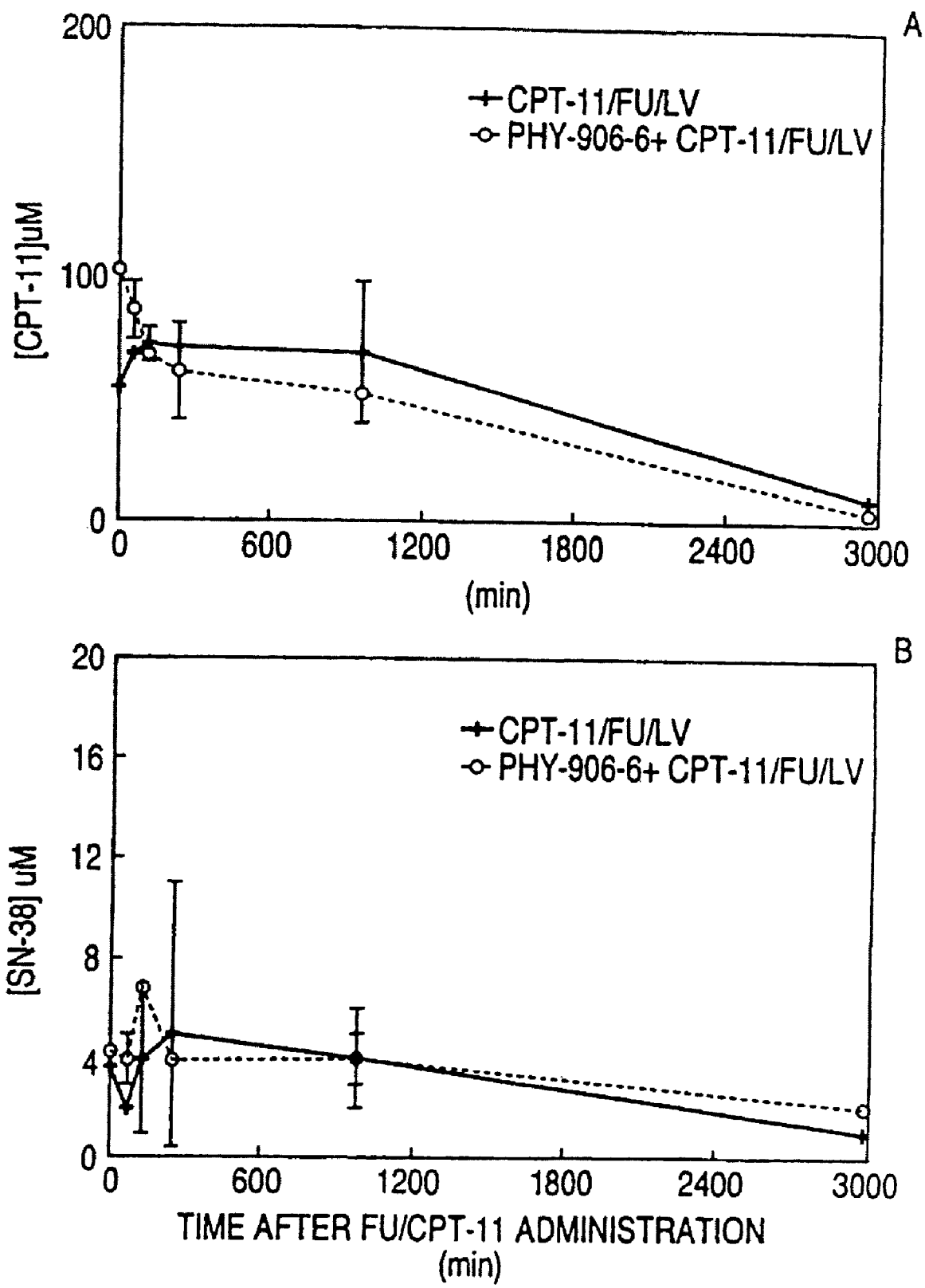
FIG. 12 A-B. Pharmacokinetic of CPT-11/FU/LV in Tumor. PHY906-6 is the clinical batch of PHY906. SN-38 is an active metabolite of CPT-11.

The pharmacokinetic data of CPT-11/FU/LV in BID-1 mice bearing Colon 38 tumor in the presence and absence of PHY906 are shown in FIGS. 10-12. PHY906-6 is a clinical batch of PHY906, containing 10% excipient (starch).

The area under the curve (AUC) of CPT-11 in plasma increases after co-administration of PHY906 with the triple combination of CPT-11/FU/LV. There is no significant change of CPT-11 in either tumor or liver tissues after PHY906 co-administration.

SN-38, an active metabolite of CPT-11 remains unchanged in plasma, liver, or tumor.

The AUCs of FU and its nucleoside/nucleotide metabolites (FU+FUR+FUMP) in plasma or liver change after PHY906 co-administration with the triple combination of CPT-11/FU/LV.

All applications, patent, and publications referenced herein are incorporated by reference to the same extent as if each individual application, patent, and publication was specifically and individually indicated to be incorporated by reference. Specifically, the disclosures of WO 01/66123, WO 06/053049, U.S. Pat. No. 7,025,993, US 2005/0196473, and US 2003/0211180 are incorporated herein by reference in their entirety for all purposes. Furthermore, the following references and their contents are herein incorporated by reference in their entirety for all purposes:

1. Bergsland, E. K. and Venook, A. P. Hepatocellular Carcinoma [Gastrointestinal Tract]. Current Opinion in Oncology, 12: 357-361, 2000.
2. Fernandez-Zapico, M. E., Kaczynski, J. A., and Urrutia, ft. Pancreatic Cancer Research: Challenges, Opportunities, and Recent Developments. Curr Opin Gastroenterol, 18: 563-567, 2002.
3. Jemal, A., Thomas, A., Murray, T., and Thun, M. Cancer Statistics, 2002. CA Cancer J Clin, 52: 23-47, 2002.
4. Skolnick, A. A. Basic Science Focus of Third International Symposium on Liver Cancer and Hepatitis. The Journal of the American Medical Association, 276: 1457-1458, 1996.
5. Abbruzzese, J. L. New Applications of Gemcitabine and Future Directions in the Management of Pancreatic Cancer. Cancer Supplement, 95: 941-945, 2002.
6. Hertel L. W., Boder, G. B., Kroin, J. S., Rinzel, S. M., Poore, G. A., Todd, G. C., and Grindey, G. B. Evaluation of the Antitumor Activity of Gemcitabine (2',2'-Difluro-2'-deoxycytidine). Cancer Res., 50: 4417-4422, 1990.
7. Pettersson, F., Colston, K. W., and Dalgleish, A. G. Retinoic Acid Enhances the Cytotoxic Effects of Gemcitabine and Cisplatin in Pancreatic Adenocarcinoma Cells. Pancreas, 23: 273-279, 2001.
8. Philip, P. A. Gemcitabine and Platinum Combinations in Pancreatic Cancer. Cancer Supplement, 95: 908-911, 2002.
9. Schultz, R. M., Meriiman, R. L., Toth, J. E., Zimmermann, J. E., Hertel, L. W., Andis, S. L., Dudley, D. E., Rutherford, P. G., Tanzer, L. R., and Grindey, G. B. Evaluation of New Anticancer Agents against the MIA paCa-2 and PANC-1 Human Pancreatic Carcinoma Xenografts. Oncology Research, 5: 223-228, 1993.
10. Von Hoff, D. D. and Bearss, D. New drugs for patients with pancreatic cancer. Current Opinion in Oncology, 14: 621-627, 2002.
11. Bruns, C. J., Harbison, M. T., Davis, D. W., Portera, C. A., Tsan, R., McConkey, D. J., Evans, D. B., Abbruzzese, J. L., Hicklin, D. J., and Radinsky, R. Epidermal Growth Factor Receptor Blockade with C225 Plus Gemcitabine Results in Regression of Human Pancreatic Carcinoma Growing Orthotopically in Nude Mice by Antiangiogenic Mechanisms. Clinical Cancer Research, 6: 1936-1948, 2000.
12. Jacobs, A. D. Gemcitabine-Based Therapy in Pancreas Cancer: Gemcitabine-Docetaxel and Other Novel Combinations. Cancer Supplement, 95: 923-927, 2002.
13. McGinn, C. J., Lawrence, T. S., and Zalupski, M. M. On the Development of Gemcitabine-Based Chemoradiotherapy Regimens in Pancreatic Cancer. Cancer Supplement, 95: 933-940, 2002.
14. Oettle, H. and Riess, H. Gemcitabine in Combination with 5-Fluorouracil with or without Folinic Acid in the Treatment of Pancreatic Cancer. Cancer Supplement, 95: 912-92, 2002.
15. Gelmon, K., Chan, A., and Harbeck, N. The role of capecitabine in first-hue treatment for patients with metastatic breast cancer. The Oncologist. 11(suppl 1): 42-51, 2006.
16. Ershler, W. B. Capecitabine monotherapy: safe and effective treatment for metastatic breast cancer. The Oncologist. 11(4):325-35, 2006.
17. Martin, M. J. Current stage-specific chemotherapeutic options in colon cancer. Expert Rev Anticancer Ther. 5(4): 695-704, 2005.
18. Cartwright, T. H., Cohn, A., Varkey, J. A., et al, A Phase II study of oral capecitabine in patients with advanced or metastatic pancreatic cancer. J Clin Oncol. 20: 160-164, 2002,
19. Lozano, R. D., Patt, Y. Z., Hassan, M. M., Frome, A., Vauthey, J. N., Ellis, L. M., Schnirer, T. D., Brown, J. L., Abbruzzese, J. L., Wolff, R. A., and Charnsangavej, C. Oral Capecitabine (Xeloda) for the treatment of hepatobiliary cancers (hepatocellular carcinoma, cholangiocarcinoma, and gallbladder cancer), Proc Am Soc Clin Oncol. 19:1025A, 2000
20. Strumberg, D., Richly, H., Hilger, R. A., et al. Phase I clinical and pharmacokinetic study of the novel Raf kinase and vascular endothelial growth factor receptor inhibitor BAY 43-9006 in patients with advanced refractory solid tumors. J Clin Oncol. 23: 965-972, 2005
21. Abou-Alfa, G. K. Schwartz, L., Ricci, S., et al. Phase II study of sorafenib in patients with advanced hepatocellular carcinoma. J Clin Oncol, 24:4293-4300
22. ACS Cancer Facts and Figures. American Cancer Society, 2004.
23. Raymond, F., Faivre, S., Chaney, S., Woynarowski, J., and Cvitkovic, E. Cellular and Molecular Pharmacology of Oxaliplatin. Molecular Cancer Therapeutics, 1: 227-235, 2002.
24. Diggle, P. J., Liang, K. Y., and Zeger, S. L. Analysis of Longitudinal Data, 2nd ed. Oxford: Oxford Science Publications, 1994.

We claim:

1. A method of treating cancer in a mammal comprising co-administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

2. The method of claim 1, wherein the herbal preparation is administered via oral route, and the chemotherapeutic formulation is administered via oral or parenteral route.

3. The method of claim 2, wherein the herbal preparation is administered via oral route, and the chemotherapeutic formulation is administered via intravenous route.

4. The method of claim 1, wherein the herbal preparation consists of *Scutellaria baicalensis, Glycyrrhiza uralensis, Ziziphus jujuba* and *Paeonia lactiflora*, and one or more pharmaceutically acceptable carrier.

5. The method of claim 1, wherein the herbal preparation is administered before the administration of the chemotherapeutic formulation.

6. The method of claim 1, wherein the herbal preparation is administered after the administration of the chemotherapeutic formulation.

7. The method of claim 1, wherein the herbal preparation is administered concurrently with the administration of the chemotherapeutic formulation.

8. A method of relieving side effects of a chemotherapeutic compound in a mammal comprising co-administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

9. The method of claim 8, wherein the herbal preparation is administered via oral route, and the chemotherapeutic formulation is administered via oral or parenteral route.

10. The method of claim 9, wherein the herbal preparation is administered via oral route, and the chemotherapeutic formulation is administered via intravenous route.

11. The method of claim 8, wherein the herbal preparation consists of *Scutellaria baicalensis, Glycyrrhiza uralensis, Ziziphus jujuba* and *Paeonia lactiflora*, and one or more pharmaceutically acceptable carrier.

12. The method of claim 8, wherein the herbal preparation is administered before the administration of the chemotherapeutic formulation.

13. The method of claim 8, wherein the herbal preparation is administered after the administration of the chemotherapeutic formulation.

14. The method of claim 8, wherein the herbal preparation is administered concurrently with the administration of the chemotherapeutic formulation.

15. A method of enhancing anticancer activity of a chemotherapeutic compound in a mammal comprising administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

16. The method of claim 15, wherein the herbal preparation is administered via oral route, and the chemotherapeutic formulation is administered via oral or parenteral route.

17. The method of claim 16, wherein the herbal preparation is administered via oral route, and the chemotherapeutic formulation is administered via intravenous route.

18. The method of claim 15, wherein the herbal preparation consists of *Scutellaria baicalensis, Glycyrrhiza uralensis, Ziziphus jujuba* and *Paeonia lactiflora*, and one or more pharmaceutically acceptable carrier.

19. The method of claim 15, wherein the herbal preparation is administered before the administration of the chemotherapeutic formulation.

20. The method of claim 15, wherein the herbal preparation is administered after the administration of the chemotherapeutic formulation.

21. The method of claim 15, wherein the herbal preparation is administered concurrently with the administration of the chemotherapeutic formulation.

22. A method of treating cancer in a mammal comprising separately administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

23. The method of claim 22 wherein the chemotherapeutic formulation comprises 5-fluorouracil (5-FU) and leucovorin (LV).

24. The method of claim 22 wherein the chemotherapeutic formulation comprises irinotecan (CPT-11), 5-fluorouracil (5-FU), and leucovorin (LV).

25. A method of relieving side effects of a chemotherapeutic compound in a mammal comprising separately administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

26. The method of claim 25 wherein the chemotherapeutic formulation comprises 5-fluorouracil (5-FU) and leucovorin (LV).

27. The method of claim 25 wherein the chemotherapeutic formulation comprises irinotecan (CPT-11), 5-fluorouracil (5-FU), and leucovorin (LV).

28. A method of enhancing anticancer activity of a chemotherapeutic compound in a mammal comprising separately administering a therapeutically effective amount of
   i) an herbal preparation consisting essentially of *Scutellaria baicalensis, Glycyrrhiza uralensis, Ziziphus jujuba* and *Paeonia lactiflora;* and
   ii) a chemotherapeutic formulation comprising a chemotherapeutic compound selected from the group consisting of irinotecan (CPT-11), 5-fluorouracil (5-FU), etoposide (VP-16), beta-L-Dioxolane-cytidine (L-OddC), leucovorin (LV) and combinations thereof.

29. The method of claim 28 wherein the chemotherapeutic formulation comprises 5-fluorouracil (5-FU) and leucovorin (LV).

30. The method of claim 28 wherein the chemotherapeutic formulation comprises irinotecan (CPT-11), 5-fluorouracil (5-FU), and leucovorin (LV).

* * * * *